(12) United States Patent
Grass et al.

(10) Patent No.: US 10,426,417 B2
(45) Date of Patent: Oct. 1, 2019

(54) COMPUTED TOMOGRAPHY (CT) HYBRID DATA ACQUISITION

(71) Applicant: KONINKLIJKE PHILIPS N.V., Eindhoven (NL)

(72) Inventors: Michael Grass, Buchholz In der Nordheide (DE); Thomas Koehler, Norderstedt (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 165 days.

(21) Appl. No.: 15/301,513

(22) PCT Filed: Jun. 3, 2015

(86) PCT No.: PCT/IB2015/054187
§ 371 (c)(1),
(2) Date: Oct. 3, 2016

(87) PCT Pub. No.: WO2015/193761
PCT Pub. Date: Dec. 23, 2015

(65) Prior Publication Data
US 2017/0172529 A1    Jun. 22, 2017

Related U.S. Application Data

(60) Provisional application No. 62/012,607, filed on Jun. 16, 2014.

(51) Int. Cl.
*A61B 6/00*    (2006.01)
*A61B 6/03*    (2006.01)

(52) U.S. Cl.
CPC .............. *A61B 6/484* (2013.01); *A61B 6/032* (2013.01); *A61B 6/4014* (2013.01); *A61B 6/42* (2013.01);
(Continued)

(58) Field of Classification Search
CPC ............................ A61B 6/4241; A61B 6/484
See application file for complete search history.

(56) References Cited

U.S. PATENT DOCUMENTS 8,306,183 B2    11/2012    Koehler
8,532,251 B2    9/2013    Luhta
(Continued)

FOREIGN PATENT DOCUMENTS

WO    20130126296    8/2013

OTHER PUBLICATIONS

Tam, et al., "Reducing the fan-beam scanning angular range", Physics in Medicine and Biology, Institute of Physics Publishing, vol. 33, No. 8, Aug. 1, 1988.

*Primary Examiner* — Dani Fox
(74) *Attorney, Agent, or Firm* — Larry Liberchuk

(57) ABSTRACT

An imaging system (200) includes a radiation source (208) that emits radiation that traverses an examination region. The imaging system further includes a hybrid data acquisition system (212) that receives radiation that traverses the examination region. The hybrid data acquisition system includes a phase-contrast sub-portion (304) spanning a sub-portion of a full field of view. The hybrid data acquisition system further includes at least one of an integrating portion (302, 702, 804, 806, 902) or a spectral portion (402, 704, 706, 802, 1002) spanning the full field of view. The hybrid data acquisition system generates a phase-contrast signal and at least one of an integration signal or a spectral signal. The imaging system further includes a reconstructor (216) that reconstructs the phase-contrast signal and at least one of the integration single or the spectral signal to generate volumetric image data indicative of the examination region.

19 Claims, 8 Drawing Sheets

(52) U.S. Cl.
CPC .......... *A61B 6/4241* (2013.01); *A61B 6/4291* (2013.01); *A61B 6/5205* (2013.01); *G06T 2207/10081* (2013.01)

(56) References Cited

U.S. PATENT DOCUMENTS

| | | |
|---|---|---|
| 8,712,138 B2 | 4/2014 | Gleich |
| 2007/0183559 A1 | 8/2007 | Hempel |
| 2011/0142316 A1 | 6/2011 | Wang |
| 2011/0274246 A1 | 11/2011 | Maschke |
| 2012/0243658 A1 | 9/2012 | Geller |
| 2013/0028379 A1* | 1/2013 | Nelson .................. G01N 23/04 378/62 |
| 2014/0079184 A1 | 3/2014 | Das |

* cited by examiner

COMPUTED TOMOGRAPHY (CT) HYBRID DATA ACQUISITION

CROSS REFERENCE TO RELATED APPLICATIONS

This application is the U.S. National Phase application under 35 U.S.C. § 371 of International Application No. PCT/IB2015/054187, filed Jun. 3, 2015, published as WO 2015/193761 on Dec. 23, 2015, which claims the benefit of U.S. Provisional Patent Application No. 62/012,607 filed Jun. 16, 2014. These applications are hereby incorporated by reference herein.

The following generally relates to data acquisition and more particularly to a hybrid phase-contrast data acquisition system and/or method for computed tomography (CT).

With CT, contrast is obtained through the differences in the absorption cross-section of the constituents of the scanned object. This yields good results where highly absorbing structures such as bones are embedded in a matrix of relatively weakly absorbing material, for example the surrounding tissue of the human body. However, where different forms of tissue with similar absorption cross-sections are under investigation (e.g., mammography or abdominal imaging), the X-ray absorption contrast is relatively poor. Consequently, differentiating pathologic from non-pathologic tissue in an absorption radiograph obtained with a current hospital-based X-ray system remains difficult for certain tissue compositions.

Figure 1:
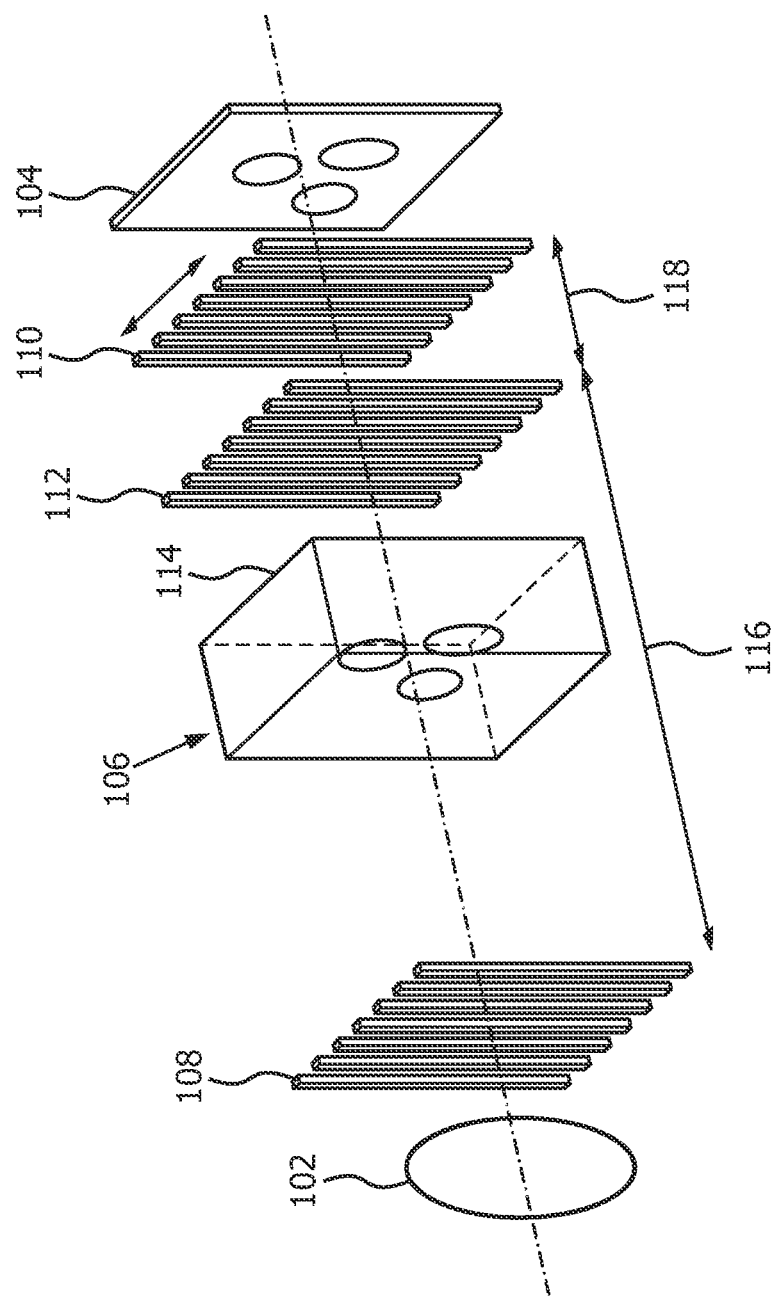

Phase-contrast imaging overcomes the above-noted contrast limitation. Generally, such imaging utilizes X-ray gratings, which allow the acquisition of X-ray images in phase contrast, which provides additional information about the scanned object. With phase-contrast imaging, an image is generated that is based on the scatter components of the X-ray radiation diffracted by the scanned object. Very slight density differences in the scanned object then can be shown at very high resolution. An example phase-contrast imaging system is discussed in patent application US 20120243658 A1, filed Dec. 3, 2010, entitled "Phase Contrast Imaging," the entirety of which is incorporated herein by reference. FIG. 1 shows an example configuration from US 20120243658 A1.

In FIG. 1, an X-ray source 102 and a detector array 104 are located opposite each other, across an examination region 106. A source grating 108 is adjacent to the source 102, an absorber (or analyzer) grating 110 is adjacent to the detector array 104, and a phase grating 112 is between an object 114 and the absorber grating 110. The source grating 108 is separated from the phase grating 112 by a distance ("l") 116. The phase grating 112 is separated from the absorber grating 110 by a distance ("d") 118, which corresponds to the Talbot distance ($d=p_1^2/8\lambda$, where $\lambda$ is the wavelength of the incident radiation). The source grating 108, the phase grating 112, and the absorber grating 110 respectively have grating line periods $p_0$, $p_1$ and $p_2$, where $p_2=1/d\ p_0$ and $p_2=\frac{1}{2}\ p_1\cdot(d+1)/1$.

The source grating 108 creates an array of individually coherent, but mutually incoherent sources. The object 114 in the beam path causes a slight refraction for each coherent subset of X-rays, which is proportional to the local phase gradient of the object. This small angular deviation results in changes of the locally transmitted intensity through the combination of the phase gratings 112 and the absorber grating 110. The phase grating 112 acts as a beam splitter and divides an incoming X-ray beam essentially into the two first diffraction orders. The diffracted beams interfere and form, in Talbot distances, linear periodic fringe patterns with a periodicity that equals half the phase grating times the geometric magnification factor defined by 1/(1+d).

Perturbations of the incident wave front, such as those induced by refraction on the object 114 in the beam, lead to local displacement of the fringes. The absorber grating 110 acts as a transmission mask for the detector array 104 and transforms local fringe positions into signal intensity variations. The detected signal profile hence contains quantitative information about the phase shift induced by the object 114. To code and extract the phase information, a phase-stepping approach has been utilized. With this approach, the absorber grating 110, relative to the phase grating 112, is translated in a transverse direction, which is perpendicular to the lines of gratings, via predetermined step size movements over a grating lines period.

At each grating step, a measurement is taken, and several (e.g., eight) grating steps and measurements are taken for a projection. For 3D acquisitions, the object 114 is rotated relative to the source 102, the gratings 108, 110 and 112, and the detector array 104, or the source 102, the gratings 108, 110 and 112, and the detector array 104 are rotated around the object 114 (over at least 180 degrees plus a fan angle), with a predetermined number of projections (e.g., 1000) acquired from different angular views of the rotation. Unfortunately, CT systems configured for phase-contrast imaging, as well as those including spectral (e.g., energy-resolving and/or photon counting) detectors, tend to be costly, relative to non-phase-contrast systems, which may render them cost-prohibitive.

Aspects described herein address the above-referenced problems and others.

The following describes a CT scanner with a hybrid data acquisition system. The hybrid data acquisition system includes a phase-contrast sub-section in connection with at least one of integrating detector section and/or an energy-resolving and/or photon counting section. As such, the CT scanner described herein allows for phase-contrast imaging at a reduced cost relative to a phase-contrast CT scanner with a full (non-hybrid) phase-contrast data acquisition system.

In one aspect, an imaging system includes a radiation source that emits radiation that traverses an examination region. The imaging system further includes a hybrid data acquisition system that receives radiation that traverses the examination region. The hybrid data acquisition system includes a phase-contrast sub-portion spanning a sub-portion of a full field of view. The hybrid data acquisition system further includes at least one of an integrating portion or a spectral portion spanning the full field of view. The hybrid data acquisition system generates a phase-contrast signal and at least one of an integration signal or a spectral signal. The imaging system further includes a reconstructor that reconstructs the phase-contrast signal and at least one of the integration single or the spectral signal to generate volumetric image data indicative of the examination region.

In another aspect, a method includes transmitting, with a radiation source, radiation through an examination region. The method further includes receiving, with a hybrid data acquisition system, radiation that traverses the examination region. The hybrid data acquisition system includes at least one of an integrating portion spanning a full field of view or a spectral portion spanning the full field of view and a phase-contrast sub-portion spanning a sub-portion of the field of view. The hybrid data acquisition system generates at least one of an integration signal or a spectral signal and a phase-contrast signal.

In another aspect, an imaging system includes a hybrid data acquisition system that receives radiation that traverses the examination region. The hybrid data acquisition system includes at least two different types of detector sub-systems, including a phase-contrast detector sub-system and a non-phase-contrast detector sub-system.

The invention may take form in various components and arrangements of components, and in various steps and arrangements of steps. The drawings are only for purposes of illustrating the preferred embodiments and are not to be construed as limiting the invention.

FIG. 1 illustrates a prior art phase-contrast data acquisition system.

Figure 2:
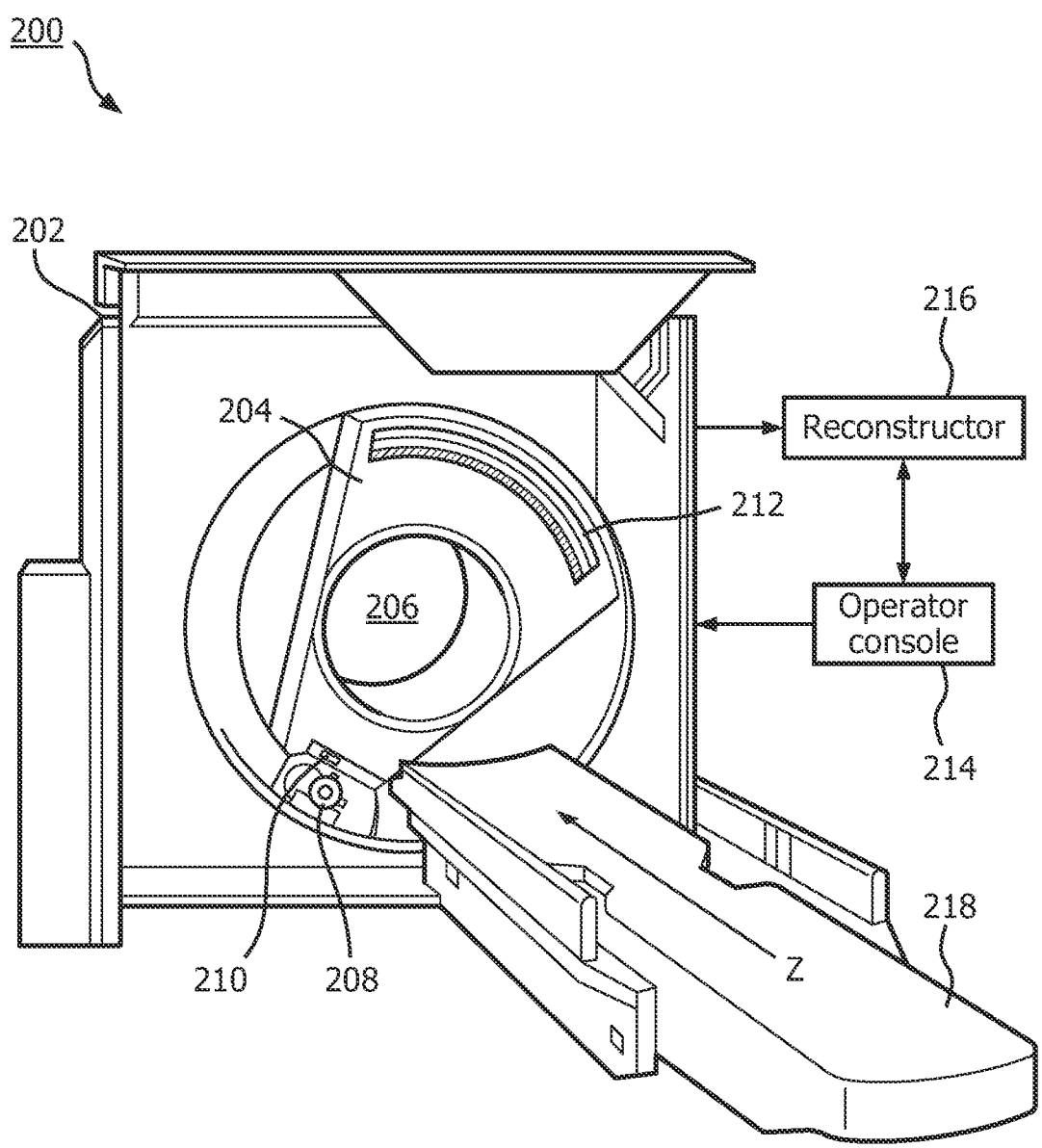

FIG. 2 schematically illustrates an imaging system with a hybrid data acquisition system that includes at least a phase-contrast sub-portion.

Figure 3:
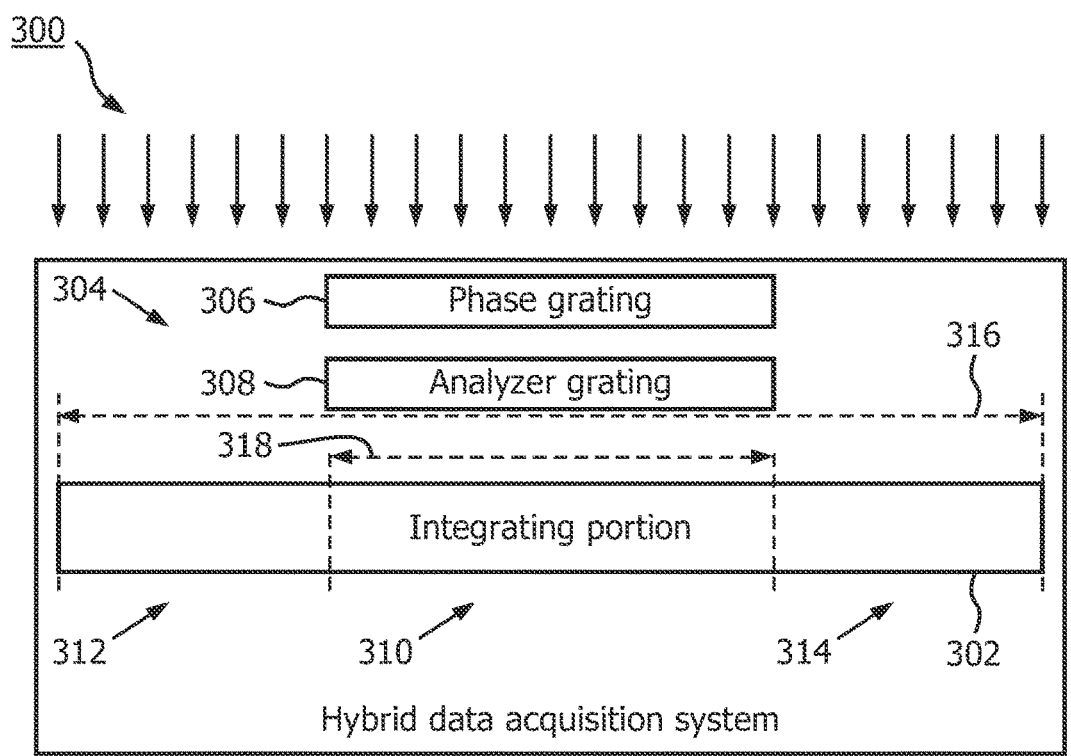

FIG. 3 schematically illustrates an example of the hybrid data acquisition system with a symmetrically located phase-contrast portion and an integrating portion.

Figure 4:
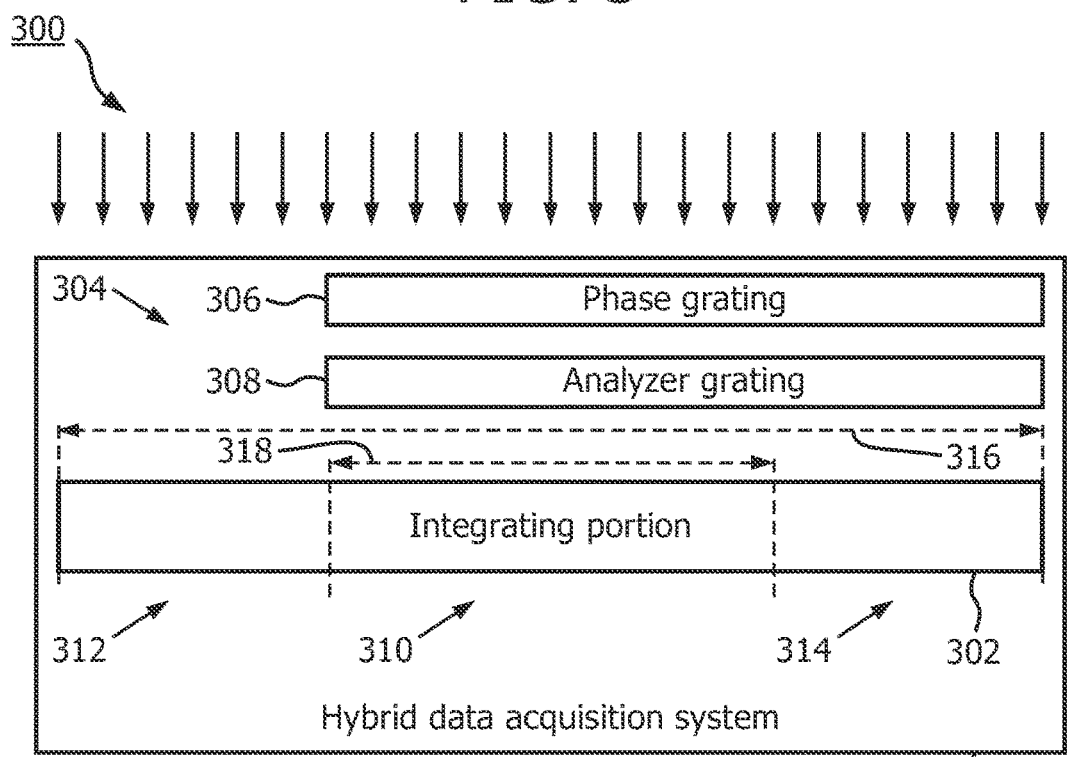

FIG. 4 schematically illustrates another example of the hybrid data acquisition system with a symmetrically located phase-contrast portion and an integrating portion.

Figure 5:
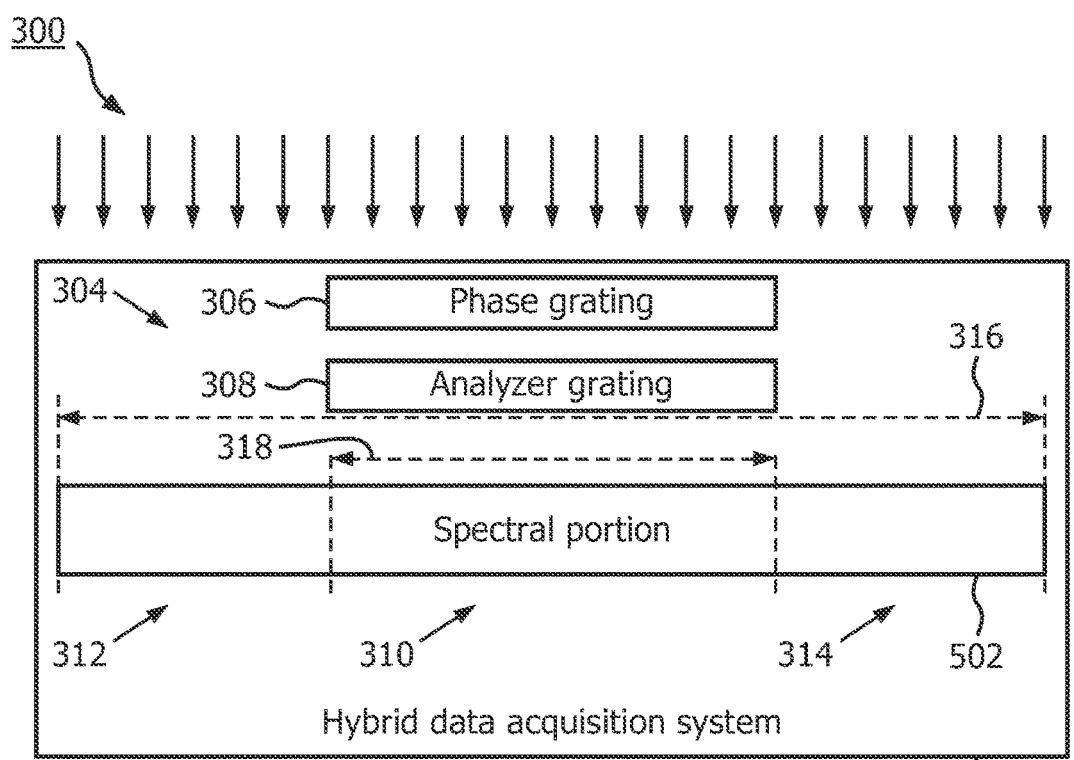

FIG. 5 schematically illustrates another example of the hybrid data acquisition system with a symmetrically located phase-contrast portion and a spectral portion.

Figure 6:
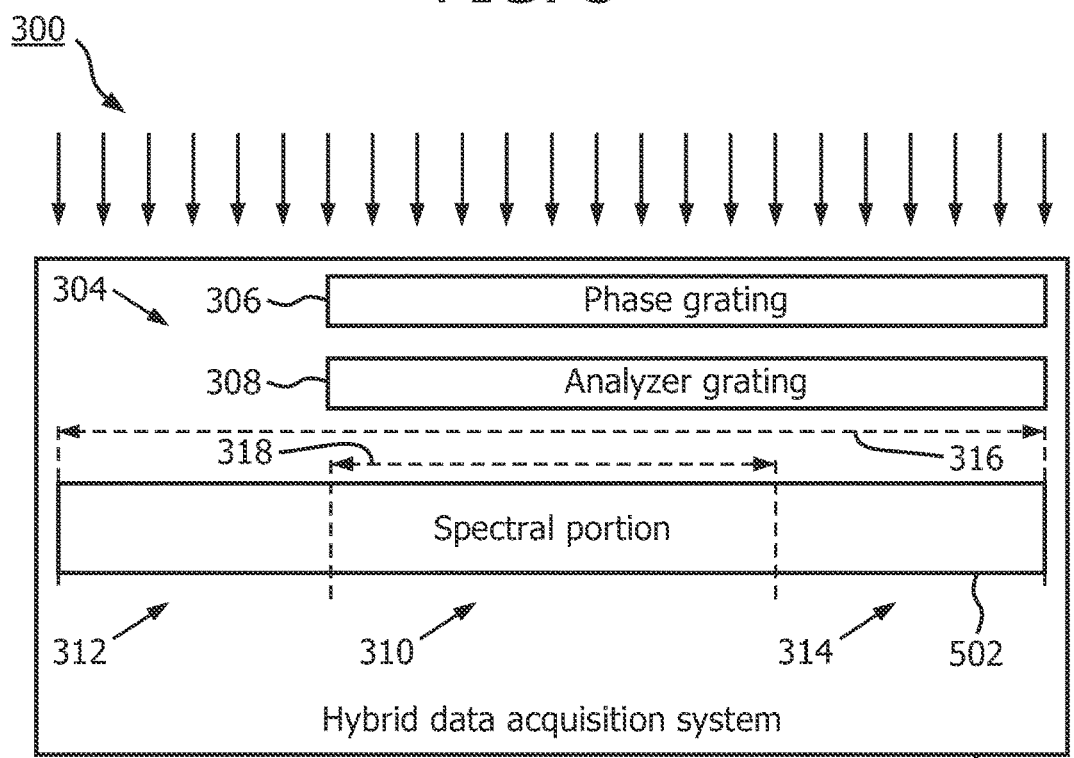

FIG. 6 schematically illustrates another example of the hybrid data acquisition system with an asymmetrically located phase-contrast portion and a spectral portion.

Figure 7:
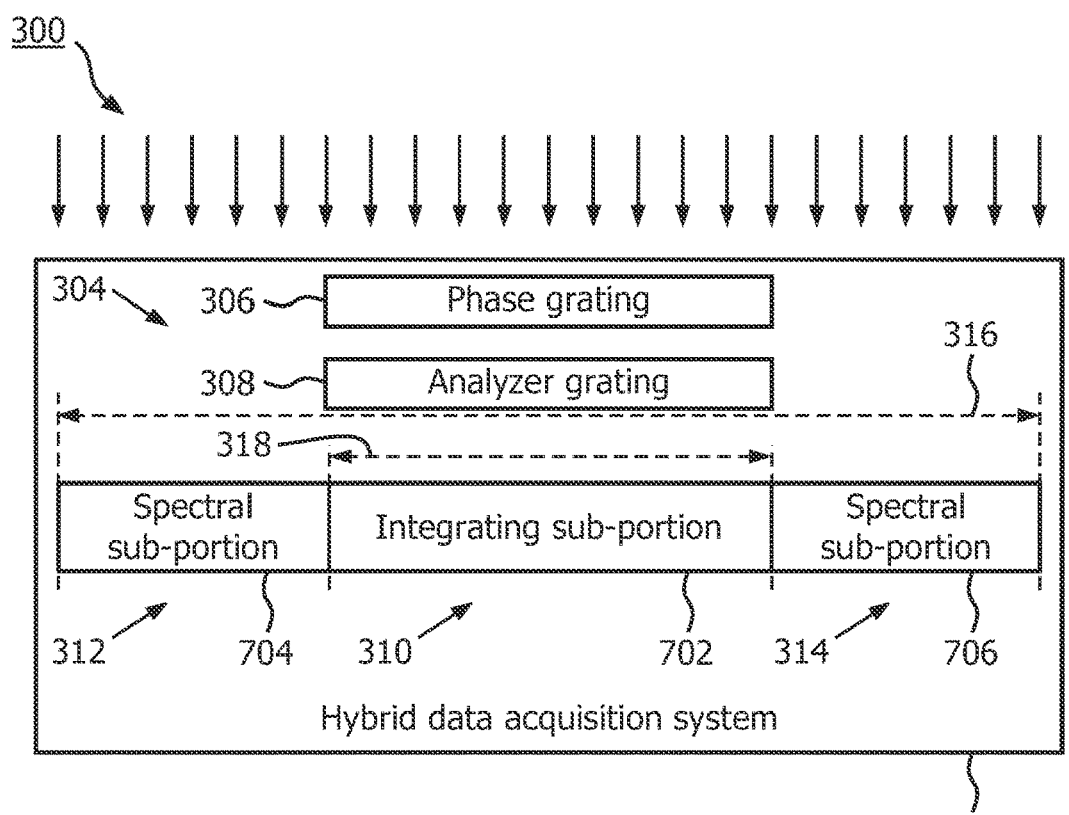

FIG. 7 schematically illustrates another example of the hybrid data acquisition system with a symmetrically located phase-contrast portion and an integrating sub-portion and spectral sub-portions.

Figure 8:
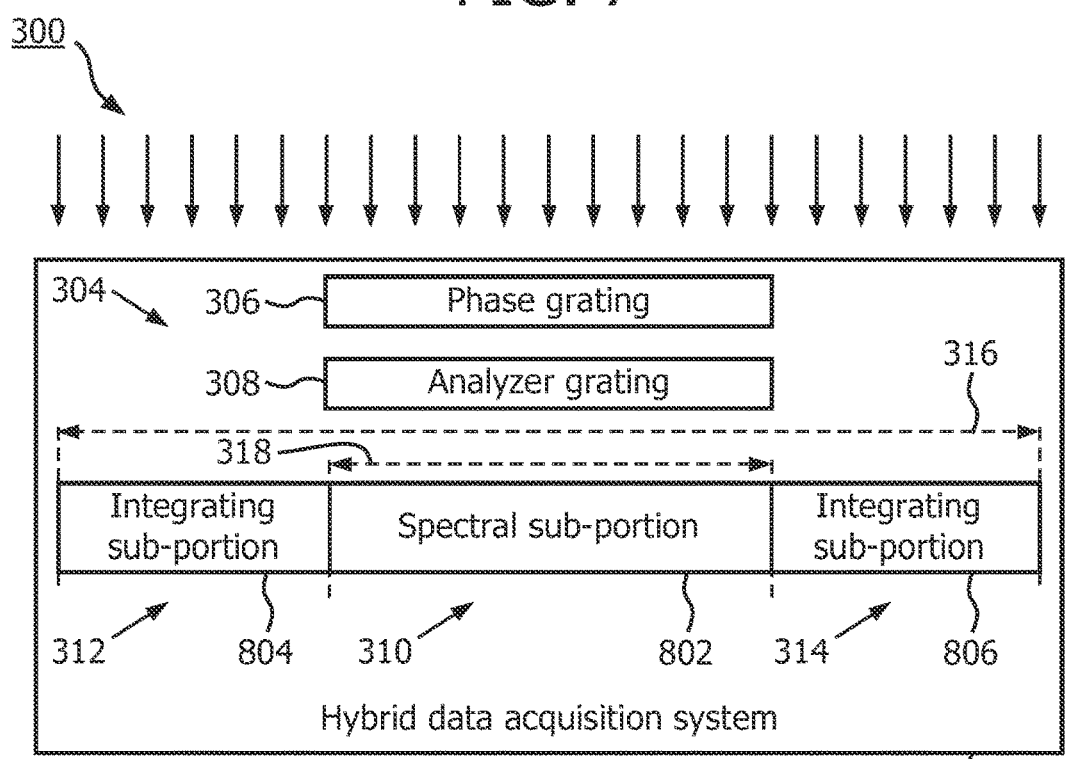

FIG. 8 schematically illustrates another example of the hybrid data acquisition system with a symmetrically located phase-contrast portion and a spectral sub-portion and integrating sub-portions.

Figure 9:
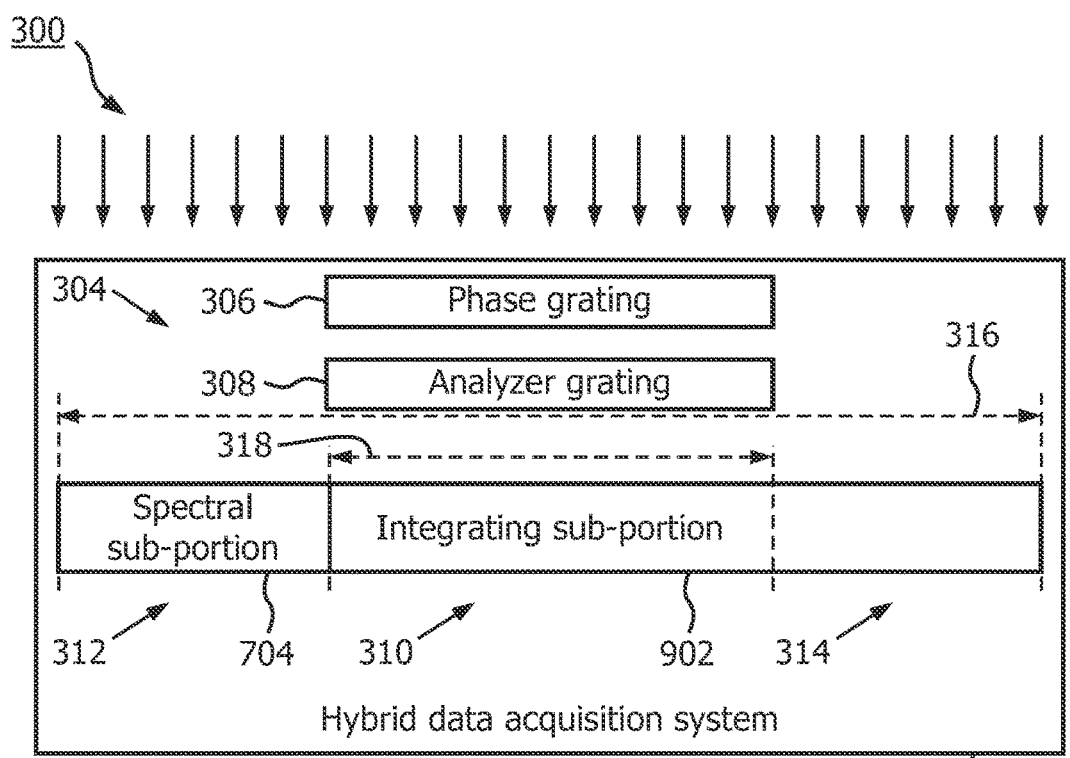

FIG. 9 schematically illustrates another example of the hybrid data acquisition system with a symmetrically located phase-contrast portion covering a sub-portion of the integrating sub-portion and none of the spectral sub-portion.

Figure 10:
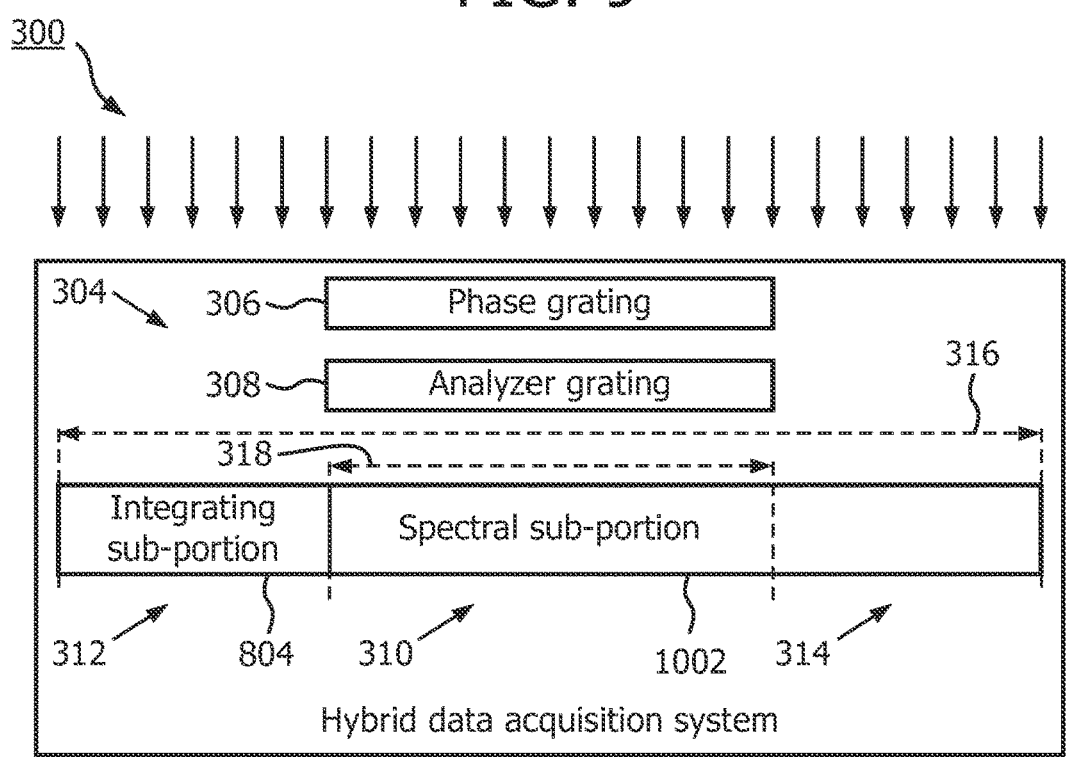

FIG. 10 schematically illustrates another example of the hybrid data acquisition system with a symmetrically located phase-contrast portion covering a sub-portion of the spectral sub-portion and none of the integrating sub-portion.

Figure 11:
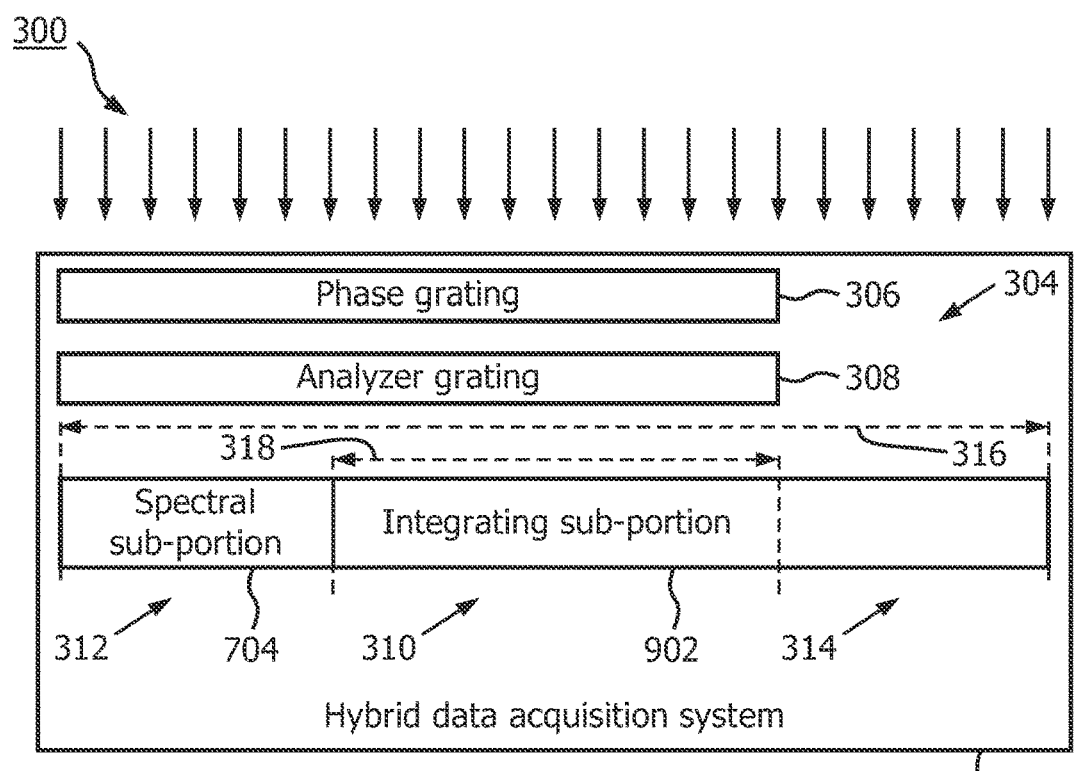

FIG. 11 schematically illustrates another example of the hybrid data acquisition system with an asymmetrically located phase-contrast portion covering the spectral sub-portion and a sub-portion of the integrating sub-portion.

Figure 12:
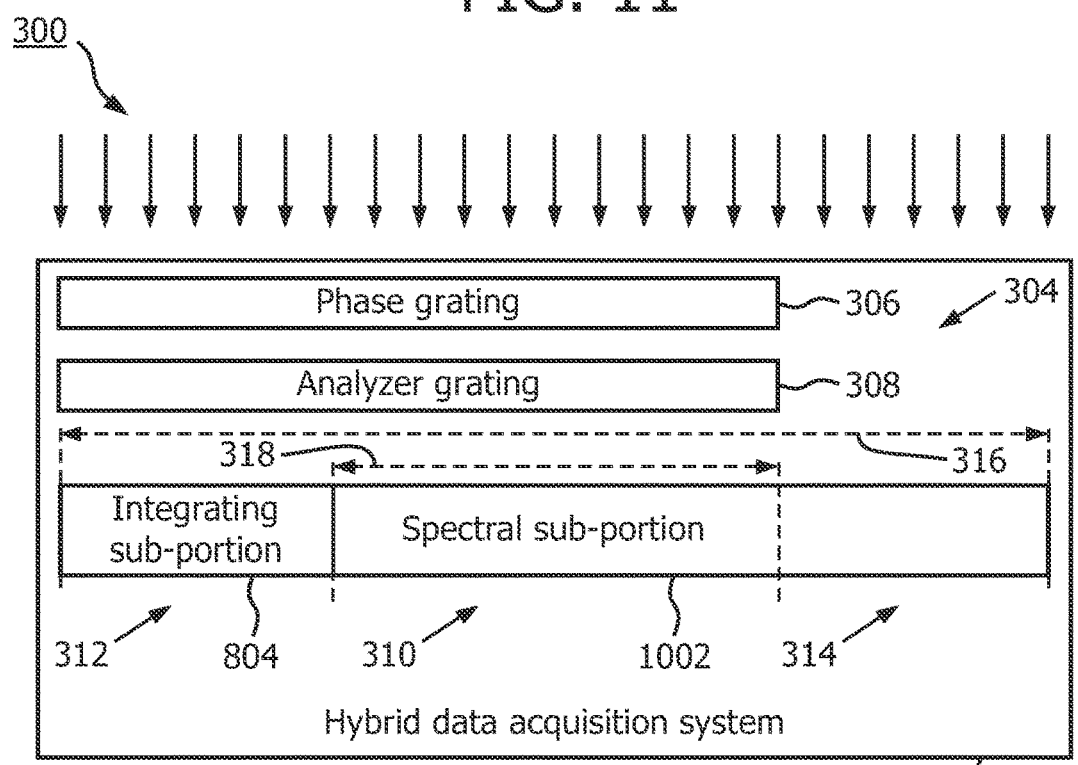

FIG. 12 schematically illustrates another example of the hybrid data acquisition system with an asymmetrically located phase-contrast portion covering the integrating sub-portion and a sub-portion of the spectral sub-portion.

Figure 13:
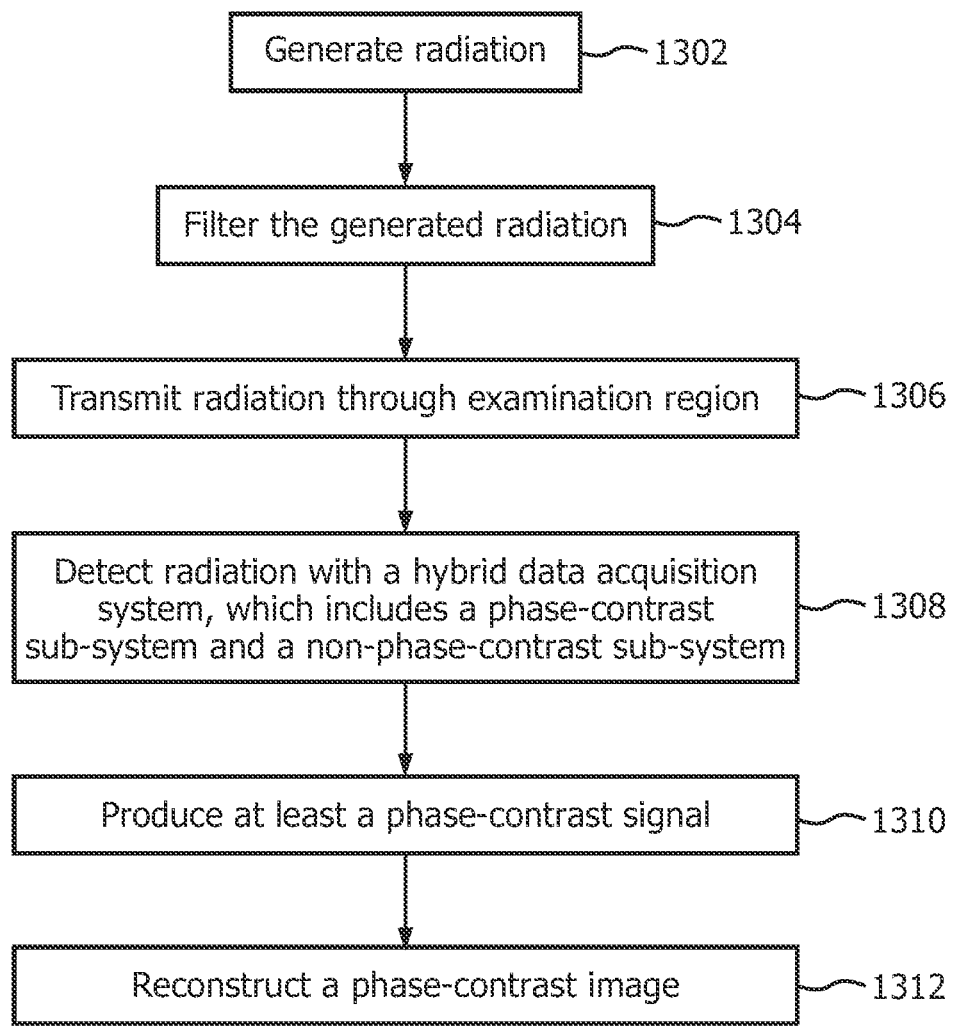

FIG. 13 illustrates a method in accordance with the embodiments described herein.

Initially referring to FIG. 2, an example imaging system 200, such as a computed tomography (CT) scanner, is schematically illustrated.

A rotating gantry 204 is rotatably supported by a stationary gantry 202 and rotates around an examination region 206 about a longitudinal or z-axis. A radiation source 208, such as an x-ray tube, is rotatably supported by the rotating gantry 204, and rotates with the rotating gantry 204 and emits radiation that traverses the examination region 206 and a portion of a subject or object therein. A source grating 210 is disposed adjacent the source 208 and filters a sub-portion of the radiation beam so that the radiation traversing the examination region 206 includes at least a sub-portion with individually coherent, but mutually incoherent rays. Where the radiation source 208 produces such rays, the source grating 210 can be omitted.

A hybrid data acquisition system 212 is located opposite the radiation source 208, across the examination region 206. The hybrid data acquisition system 212 includes a one or two dimensional array with a plurality of rows of detector pixels that extend along the z-axis direction. The hybrid data acquisition system 212 detects radiation traversing the examination region 206 and generates signals or projection data indicative thereof. As described in greater detail below, in one instance, the hybrid data acquisition system 212 includes different detection portions including a phase-contrast imaging sub-portion in connection with an integrating portion, a spectral portion, or an integrating sub-portion(s) and a spectral sub-portion(s). In general, a number of detector pixel columns that are not covered by the phase-contrast imaging sub-portion is at least one, but less than all.

The integrating portion/sub-portions generate an absorption projection: $p_{absorb}(u,v,\theta)$ with u/v being the row/column coordinate and $\theta$ the projection angle. The spectral portion/sub-portions generate a photoelectric effect projection: $p_{photo}(u,v,\theta)$, a Compton effect projection: $p_{compton}(u,v,\theta)$, an absorption projection: $p_{absorb}(u,v,\theta)$ (combined result of the former two), and/or projections with the relative contribution per chosen basis function. Two or more basis functions can be extracted when if the spectral detector includes two or more channels. The phase-contrast sub-portion generates an absorption projection: $p_{absorb}(u,v,\theta)$, a differential phase projection: $p_{phase}(u,v,\theta)$, and a dark field projection: $P_{dark}(u,v,\theta)$. The phase projection and the Compton projection are related: $p_{phase}(u,v,\theta)=K*p_{compton}(u,v,\theta)$.

A computing system serves as an operator console 214 and includes a human readable output device such as a monitor and an input device such as a keyboard, mouse, etc. The console 214 allows an operator to interact with the scanner 200 via a graphical user interface (GUI) and/or otherwise. For instance, the user can employ the input device of the operator console 214 to select a phase-contrast imaging protocol, a spectral imaging protocol, and/or a non-phase-contrast, non-spectral (or conventional) imaging protocol. A reconstructor 216 reconstructs the projection data and generates volumetric data indicative thereof. A subject support 218, such as a couch, supports a subject in the examination region 206, for example, before, during and/or after scanning.

FIGS. 3-12 schematically illustrate various different configurations of the hybrid data acquisition system 212. It is to be understood that the illustrated configurations are not limiting and that other configurations are contemplated herein. As briefly discussed above in connection with FIG. 2, the source grating 210 may cover the entire field of view or only a sub-portion of the field of view. FIGS. 3-12 show a radiation beam 300, which is the beam after it has traversed the source grating 210 and the portion of the subject or object in the examination region 206. The detector array in the examples of FIGS. 3-12 are all shown planar for explanatory purposes. However, they can be focus-centered, for example, as shown in FIG. 2.

Initially referring to FIG. 3, the hybrid data acquisition system 212 includes an integrating portion 302 that spans an entire field of view. The hybrid data acquisition system 212 further includes a phase-contrast portion 304, which includes a phase grating 306 and an analyzer grating 308 disposed between the integrating portion 302 and the phase grating 306. In this example, the phase-contrast portion 304 spans a sub-portion of the field of view. In particular, the illustrated phase-contrast portion 304 is symmetrically disposed about a central region 310 of the integrating portion 302 and not about peripheral end regions 312 and 314, which are located at opposing ends of the integrating portion 302.

The illustrated example shows diameters of at least two reconstruction fields of view, including a large or full reconstruction field of view (RFOV) diameter 316 and a small or central reconstruction field of view (RFOV) diameter 318, with respect to the hybrid data acquisition system 212. With the configuration of FIG. 3, absorption projections for the full RFOV can be acquired for both 180 degree (plus a fan angle) and 360 degree scans, and phase projections and dark field projections can be acquired for the small RFOV for both 180 degree (plus a fan angle) and 360 degree scans.

In FIG. 3, a length of the phase-contrast portion 304 is configured such that a complete set of phase-contrast projections can be obtained for the small field RFOV for certain objects such as the head, the heart, etc. for a scan that covers at least a 180 degree (plus a fan angle). For objects larger than the small RFOV, the phase-contrast projections will be incomplete, and the corresponding images for phase and dark field will only cover the small RFOV. Image reconstruction from these partial projections may lead to truncation artifacts that will manifest in the images, e.g. when filtered back projection type of reconstruction is used. A non-limiting example of such a small field of view is on the order of about two hundred and fifty millimeters in diameter.

Turning to FIG. 4, the hybrid data acquisition system 212 includes the integrating portion 302, which spans the entire field of view. The hybrid data acquisition system 212 further includes the phase-contrast portion 304 with the phase grating 306 and the analyzer grating 308 disposed between the integrating portion 302 and the phase grating 306. However, in this example, the phase-contrast portion 304 is asymmetrically disposed about the integrating portion 302, spanning the central region 310 and the peripheral end region 314. In a variation, not shown, the phase-contrast portion 304 is asymmetrically disposed about the integrating portion 302, spanning the central region 310 and the peripheral end region 312. Absorption projections for the full RFOV can be obtained for both 180 degree (plus a fan angle) and 360 degree scans, and phase projections and dark field projections can be obtained for the small RFOV for 180 degree (plus a fan angle) scans and for the large RFOV for 360 degree scans.

Next at FIG. 5, the hybrid data acquisition system 212 includes a spectral portion 502, which spans the entire field of view. The hybrid data acquisition system 212 further includes the phase-contrast portion 304 with the phase grating 306 and the analyzer grating 308 disposed between the spectral portion 502 and the phase grating 306. The phase-contrast portion 304 is symmetrically disposed about the central region 310, similar to FIG. 3. Photoelectric effect projections and Compton projections for the full RFOV can be acquired for both 180 degree (plus a fan angle) and 360 degree scans. Phase projections can be obtained for the large RFOV for both 180 degree (plus a fan angle) scans and 360 degree scans. Dark field projections can be acquired for the small RFOV for both 180 degree (plus a fan angle) scans and 360 degree scans. Absorption projections for the full RFOV can be derived by combining the photoelectric effect projections and Compton projections.

In FIG. 6, the hybrid data acquisition system 212 includes the spectral portion 502, which spans the entire field of view. The hybrid data acquisition system 212 further includes the phase-contrast portion 304 with the phase grating 306 and the analyzer grating 308 disposed between the spectral portion 502 and the phase grating 306. The phase-contrast portion 304 is asymmetrically disposed about the spectral portion 502, spanning the central region 310 and the peripheral end region 314. In a variation, not shown, the phase-contrast portion 304 is asymmetrically disposed about the spectral portion 502, spanning the central region 310 and the peripheral end region 312.

With FIG. 6, photoelectric effect projections and Compton projections for the full RFOV can be acquired for both 180 degree (plus a fan angle) and 360 degree scans. Phase projections can be acquired for the large RFOV for both 180 degree (plus a fan angle) and 360 degree scans. Dark field projections can be acquired for the small RFOV for 180 degree (plus a fan angle) scans and for the large RFOV for 360 degree scans. Absorption projections for the full RFOV can be derived for both 180 degree and 360 degree scans by combining the photoelectric effect projections and Compton projections.

Referring now to FIG. 7, the hybrid data acquisition system 212 includes a central integrating sub-portion 702 and peripheral spectral portions 704 and 706, which are disposed adjacent to integrating sub-portion 702, forming a contiguous detector array that spans the entire field of view, with each of the sub-portions 702-706 making up only a sub-portion of the detector array. The hybrid data acquisition system 212 further includes the phase-contrast portion 304 with the phase grating 306 and the analyzer grating 308 disposed between the integrating sub-portion 702 and the phase grating 306. The phase-contrast portion 304 is symmetrically disposed about the integrating sub-portion 702, not covering the spectral portions 704 and 706. Absorption projections and phase projections for the full RFOV can be obtained for both 180 degree (plus a fan angle) and 360 degree scans, and dark field projections can be obtained for the small RFOV for 180 degree (plus a fan angle) scans and for the large RFOV for 360 degree scans.

With this configuration, data truncation will occur at both sides of the phase-contrast for the full field of view. For example, phase-contrast data truncation will occur at the peripheral regions 312 and 314 of the full field of view. When combining the phase-contrast signal from in the central region 310 and the spectral signal from the peripheral regions 312 and 314, at least scatter information can be derived from both modalities. That is, a Compton image can be generated from spectral signal and the phase-contrast signal as both represent the electron density. As such, the truncation at the peripheral regions 312 and 314 can be mitigated.

The embodiment shown in FIG. 8 is substantially similar to that of FIG. 7, except the central sub-portion of the detector array is a spectral portion 802 and the peripheral sub-portions of the detector array includes integrating sub-portions 804 and 806. Absorption projections for the full RFOV can be obtained for both 180 degree (plus a fan angle) and 360 degree scans, and phase projections, dark field projections, photoelectric projections, and Compton projections can be obtained for the small RFOV for both 180 degree (plus a fan angle) and 360 degree scans.

FIG. 9 is substantially similar to that of FIG. 7, except that an integrating sub-portion 902 spans the central region 310 and the peripheral region 314. Absorption projections for the full RFOV can be obtained for both 180 degree (plus a fan angle) and 360 degree scans, and phase projections and dark field projections can be obtained for the small RFOV for both 180 degree (plus a fan angle) and 360 degree scans.

FIG. 10 is substantially similar to that of FIG. 8, except that a spectral portion 1002 spans the central region 310 and the peripheral region 314. In FIGS. 9 and/or 10, the integrating sub-portion 902 and/or the spectral portion 1002 can alternatively span the central region 310 and the peripheral region 312. Absorption projections for the full RFOV can be obtained for both 180 degree (plus a fan angle) and 360 degree scans, phase and Compton projections can be obtained for the full RFOV for 360 degree scans, phase and Compton projections can be obtained for the small RFOV for 180 degree (plus a fan angle) scans, and dark field projections and photoelectric projections can be obtained for the small RFOV for both 180 degree (plus a fan angle) and 360 degree scans.

FIG. 11 is substantially similar to that of FIG. 9, except that the phase-contrast portion 304 is asymmetrically disposed and covers the entire spectral portion 704 and only a sub-portion of the integrating sub-portion 902. Absorption projections for the full RFOV can be obtained for both 180 degree (plus a fan angle) and 360 degree scans, phase and dark field projections can be obtained for the full RFOV for 360 degree scans, and phase and dark field projections can be obtained for the small RFOV for 180 degree (plus a fan angle) scans.

FIG. 12 is substantially similar to that of FIG. 10, except that the phase-contrast portion 304 is asymmetrically disposed and covers the entire integrating sub-portion 902 and only a sub-portion of the spectral sub-portion 1002. Absorption projections and phase projections for the full RFOV can be obtained for both 180 degree (plus a fan angle) and 360 degree scans, dark field projections and photoelectric projections can be obtained for the full RFOV for 360 degree scans, and dark field projections and photoelectric projections can be obtained for the small RFOV for 180 degree (plus a fan angle) scans.

Again, FIGS. 3-12 schematically illustrate non limiting examples, and other configurations are contemplated herein. For example, in another instance, the hybrid data acquisition system 212 includes more than to two spectral sub-portions and/or integrating portions. In this instance, two or more of the spectral sub-portions can be interlaced with two or more of the integrating portions. In yet another instance, the hybrid data acquisition system 212 can include more than one phase-contrast portion 304.

FIG. 13 illustrates a method in accordance with the embodiments described herein.

It is to be appreciated that the ordering of the below acts is for explanatory purposes and not limiting. As such, other orderings are also contemplated herein. In addition, one or more of the acts may be omitted and/or one or more other acts may be included.

At 1302, radiation is generated with a radiation source.

At 1304, at least a sub-portion of the generated radiation is filtered by a source grating disposed adjacent to the radiation source, between the radiation source and examination region. As described herein, the source grating creates an array of individually coherent, but mutually incoherent sources. Where the radiation source generates such sources, act 1304 can be omitted.

At 1306, the radiation beam traverses the examination region, including a subject or object disposed therein.

At 1308, a hybrid data acquisition system detects radiation traversing the examination region and the subject or object disposed therein. As described herein, the hybrid data acquisition system includes at least two different types of detector sub-systems, including a phase-contrast detector sub-system and a non-phase-contrast detector sub-system, which may include an integrating portion or sub-portion and a spectral portion or sub-portion.

At 1310, the hybrid data acquisition system produces at least a phase-contrast signal. The hybrid data acquisition system may also produce an integrating signal and/or a spectral signal.

At 1312, the phase-contrast signal is reconstructed to produce a phase-contrast image. Where the hybrid data acquisition system also produces an integrating signal and/or a spectral signal, the signals can be combined and then reconstructed and/or individually reconstructed and then combined, and/or integrating signal and/or a spectral images can be reconstructed.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
    a radiation source configured to emit radiation that traverses an examination region;
    a hybrid data acquisition system configured to receive radiation that traverses the examination region, the hybrid data acquisition system, including: a phase-contrast sub-portion spanning a sub-portion of a full field of view; and an integrating portion and a spectral portion, which in aggregate, span the full field of view, wherein the hybrid data acquisition system is configured to generate a phase-contrast signal, an integration signal, and a spectral signal; and
    a reconstructor configured to reconstruct the phase-contrast signal and at least one of the integration signal or the spectral signal to generate volumetric image data indicative of the examination region.

2. The imaging system of claim 1, wherein the phase-contrast sub-portion is symmetrically disposed about a central region of the hybrid data acquisition system.

3. The imaging system of claim 1, wherein the spectral portion is disposed at peripheral regions and the integrating portion is disposed about a central region, which is between the peripheral regions.

4. The imaging system of claim 1, wherein the integrating portion is disposed at peripheral regions and the spectral portion is disposed about a central region, which is between the peripheral regions.

5. The imaging system of claim 3, wherein the phase-contrast sub-portion is symmetrically disposed about the central region.

6. The imaging system of claim 3, wherein the phase-contrast sub-portion is asymmetrically disposed, covering the central region and one of the peripheral regions.

7. The imaging system of claim 1, wherein the spectral portion and the integrating portion are adjacent to each other and located at opposing ends.

8. The imaging system of claim 7, wherein the spectral portion includes a spectral sub-portion with a first length and the integrating portion includes an integrating sub-portion with a second length, and the first length is longer than the second length.

9. The imaging system of claim 7, wherein the spectral portion includes a spectral sub-portion with a first length and the integrating portion includes an integrating sub-portion with a second length, and the first length is shorter than the second length.

10. The imaging system of claim 8, wherein the phase-contrast sub-portion is symmetrically disposed about the central region and over only one of the spectral sub-portion or the integrating sub-portion.

11. The imaging system of claim 8, wherein the phase-contrast sub-portion is asymmetrically disposed about the central region and over at least a sub-portion of the spectral portion or the integrating portion.

12. The imaging system of claim 1, wherein the reconstructor is configured to generate a Compton scatter image from the spectral signal and to combine the Compton scatter image with a phase-contrast image generated from the phase-contrast signal.

13. The imaging system of claim 1, wherein the phase-contrast signal includes a truncation error and the reconstructor is configured to reduce the truncation error with the spectral signal.

14. A method, comprising:
transmitting, with a radiation source, radiation through an examination region; and
receiving, with a hybrid data acquisition system, radiation that traverses the examination region,
wherein the hybrid data acquisition system, includes:
a first portion spanning a full field of view, wherein the first portion includes an integrating sub-portion and a spectral sub-portion; and
a phase-contrast sub-portion spanning a sub-portion of the field of view,
wherein the hybrid data acquisition system generates an integration signal, a spectral signal and a phase-contrast signal.

15. The method of claim 14, further comprising:
acquiring data over at least one three hundred and sixty degrees; and
reconstructing a phase-contrast image for the full field of view.

16. The method of claim 14, further comprising:
acquiring data over at least one hundred and eighty degrees plus a fan angle; and
reconstructing a phase-contrast image for a sub-portion of the full field of view.

17. The method of claim 16, further comprising:
generating a Compton scatter image from the spectral signal; and
combining the Compton scatter phase-contrast image to create a derived phase-contrast image for the full field of view.

18. The method of claim 14, further comprising:
correcting a truncation error of the phase-contrast signal with the spectral signal.

19. An imaging system, comprising:
a hybrid data acquisition system configured to receive radiation that traverses the examination region, the hybrid data acquisition system, including: at least two different types of detector sub-systems, including a phase-contrast detector sub-system and a non-phase-contrast detector sub-system with both an integrating sub-portion and a spectral sub-portion.

* * * * *